United States Patent [19]

Kelada et al.

[11] 4,265,857
[45] May 5, 1981

[54] IN-LINE DISTILLATION SYSTEM

[75] Inventors: Nabih P. Kelada, Glen Ellyn; Cecil Lue-Hing, Chicago; David T. Lordi, LaGrange, all of Ill.

[73] Assignee: The Metropolitan Sanitary District of Greater Chicago, Chicago, Ill.

[21] Appl. No.: 961,162

[22] Filed: Nov. 16, 1978

[51] Int. Cl.$^3$ .................... B01D 3/00; B01L 11/00; G01N 31/06; G01N 35/08
[52] U.S. Cl. .................... 422/101; 23/230 PC; 202/182; 202/197; 203/DIG. 2; 422/80; 422/82
[58] Field of Search ............... 202/161, 162, 182, 197; 203/40, DIG. 3; 422/80, 82, 101; 23/230 PC

[56] References Cited

U.S. PATENT DOCUMENTS

| | | | |
|---|---|---|---|
| 1,887,126 | 11/1932 | Grossmann | 422/101 |
| 3,169,912 | 2/1965 | Ferrari et al. | 422/101 X |
| 3,395,083 | 7/1968 | Gilmont | 422/101 X |
| 3,794,566 | 2/1974 | Raal | 202/197 X |
| 3,854,877 | 12/1974 | Csaky | 23/230 PC |
| 3,907,683 | 9/1975 | Gilmont | 202/197 X |

OTHER PUBLICATIONS

Advances in Auto. Analysis, Technicon Inter. Congress 1976, vol. 2, Industrial Symposia, 1977, pp. 73-82, Kelada et al.
Will Thin Film Tech. Spread in Process Ind., Process Engin. 1/74.
Det. of Nanogram Quantities of Simple & Complex Cyanides in Water, Analy. Chem., vol. 44, No. 11, Sep. 1972, pp. 1845-1849.

Primary Examiner—Michael S. Marcus
Attorney, Agent, or Firm—Bernard L. Kleinke

[57] ABSTRACT

An in-line distillation system for separating volatile components entrained in a liquid includes a distillation device for separating the volatile components from the liquid. A distribution device is connected in fluid communication with the outlet of the distillation and has a first conduit portion for flowing the separated volatile component from the outlet of the distillation device, and a second conduit portion for flowing the liquid from the outlet of the distillation device. A trap device resists the flow of the separated volatile component from entering the second conduit and thus forces the flow of volatile component into the first conduit. The trap device includes a reservoir container device for receiving liquid from the second container. An outlet at the upper portion of the container device spaced by a substantial distance above the exit end of said second conduit permits the flow of liquid therefrom.

9 Claims, 4 Drawing Figures

U.S. Patent — May 5, 1981 — 4,265,857
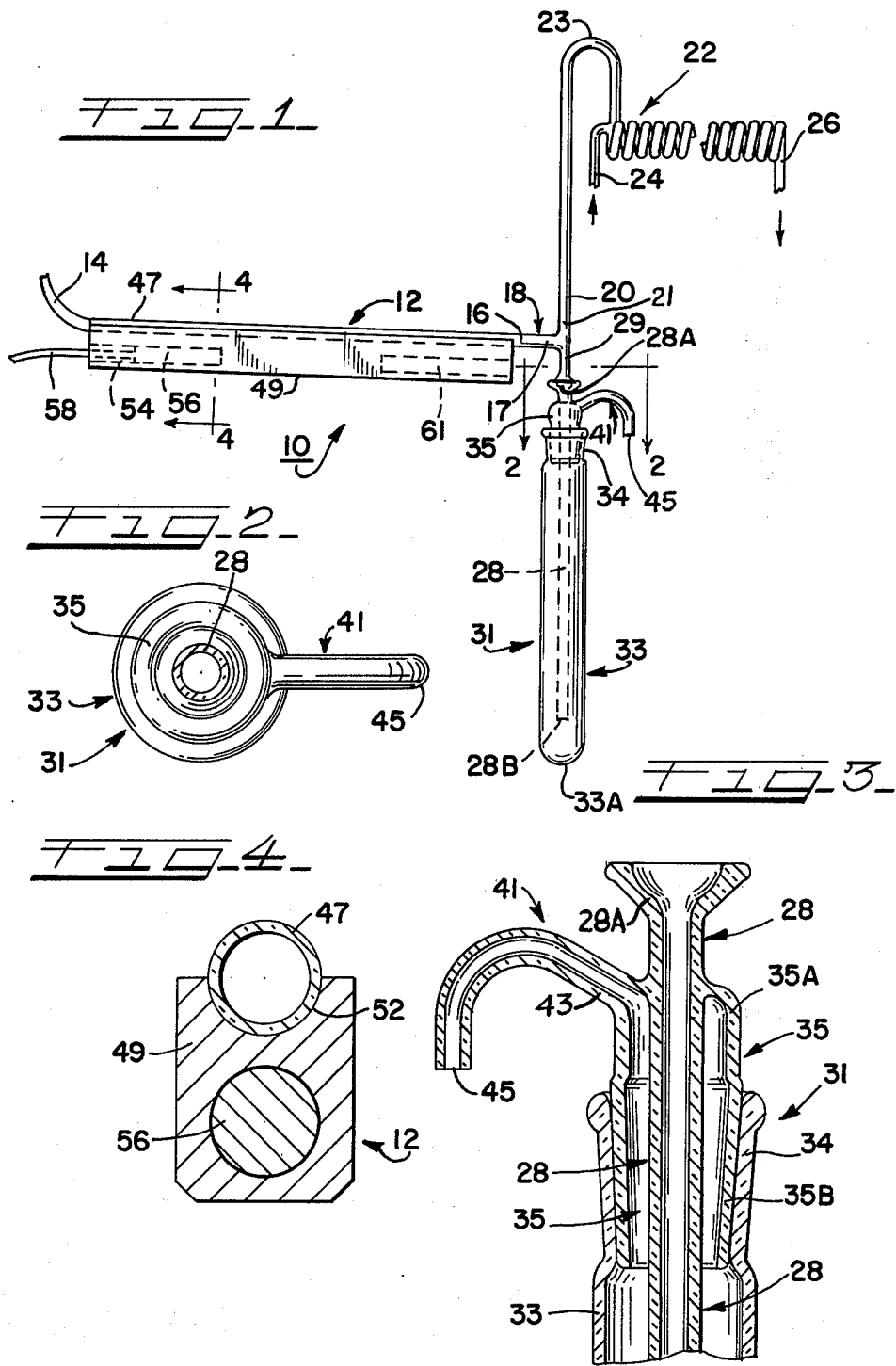

IN-LINE DISTILLATION SYSTEM

BRIEF SUMMARY OF THE INVENTION

The present invention relates in general to an in-line distillation system, and it more particularly relates to an in-line distillation system for separating volatile components entrained in a liquid for analysis purposes.

Continuous in-line analysis of fluid samples is becoming increasingly more important to enable large scale monitoring of the quality of liquids, such as water. In this regard, the water quality of lakes, rivers and streams are continuously monitored by analyzing water samples for unwanted and undesirable components, such as cyanides, phenols and the like in both fresh water and waste water. In order to analyze large numbers of samples in a convenient and efficient manner, automatic systems, such as automatic in-line thin-film distillation systems, have been designed and are being used for these purposes. For example, reference may be made to the following publications: (1) an article by David Guttridge et al, entitled "Will Thin Film Technology Spread in the Process Industry?," *Process Engineering*, the first part of which was published in January of 1974 at page 94, (2) an article by Peter D. Goulden et al, entitled "Determination of Nanograms Quantities of Simple and Complex Cyanides in Water" appearing in *Analytical Chemistry*, Vol. 44, pages 1845 through 1849, September 1972, and (3) an article by Nabih P. Kelada et al, entitled "Cyanides Species Methodology in Water, Waste Water and Sediments," appearing in *Advances in Automatic Analysis, Technicon International Congress* 1976, Vol. 2, *Industrial Symposia*, 1977, at pages 73 through 82. In the thin-film distillation systems disclosed therein, volatile components entrained in a liquid are separated therefrom for testing purposes in a continuous automated process. The separated volatile components are collected and absorbed in suitable solutions and subjected to further analysis as desired. The liquid flowing from the thin-film distillation apparatus may be suitably disposed of by flowing it into a drain line, and devices, such as conventional traps comprising a reversely bent tube are provided to resist the flow of the volatile component into the liquid drain line, so that substantially the entire volatile component can be captured for test purposes without losing any of it down the drain line. However, while such continuous thin-film distillation processes have been employed successfully for some applications, they have tended, in some situations, to become shut down inadvertently. Such a situation is highly undesirable for the reason that the system must be reset and restarted, and such a time-consuming operation is undesirable and unwanted. Such malfunctions have occurred when a larger than expected concentration of the volatile component exists in an unknown liquid sample, and thus the pressure due to the volatile component forces the component through the trap and into the drain line, thereby destroying the sample and causing the liquid to be forced out of the drain. In such a situation, the entire in-line thin-film distillation process must be interrupted so as to refill the trap to prevent the same condition from occurring again. Also, by employing a reversely bent tube as the trap, sediment oftentimes collects in the bottom portion of the tubing, and if such sediment does collect, the drain line can become clogged, thereby shutting down the system and requiring a time-consuming, awkward cleaning operation of the trap. Therefore, it would be highly desirable to have a new and improved thin-film distillation system which facilitates the testing for volatile components entrained in liquids in a continuous in-line system without the unwanted and undesirable delays resulting from inadvertent malfunctioning of the system and with a conveniently cleanable trap. Such a system should include a trap which is capable of correcting itself should the volatile component enter the trap, and in this regard, such a trap should be capable of refilling itself when a subsequent sample containing an expected concentration of the volatile component is distilled by the system without the need for disassembling the system and refilling the trap manually in a time-consuming operation.

Therefore, it is the principal object of the present invention to provide a new and improved continuous in-line distillation system which operates in a substantially uninterrupted manner, and which includes an easy-to-clean trap therefor.

Briefly, the above and further objects of the present invention are realized by providing an in-line distillation system, which includes a distillation device for separating the volatile components from the liquid under test. A distribution device is connected in fluid communication with the outlet of the distillation device and includes first and second conduit portions for flowing the separated volatile components from the outlet of the distillation means through the first conduit and for flowing the liquid from the outlet of the distillation device through the second conduit. A trap device resists the flow of the separated volatile components from entering the second conduit. The trap includes a container for receiving liquid from the second conduit. The container includes an outlet at the upper portion thereof spaced by a substantial distance above the exit end of the second conduit so that liquid collects in the container to impede the flow of the separated volatile component into the second conduit.

These and other objects of the present invention will become more apparent by a review of the accompanying specification and drawings, wherein:

FIG. 1 is a partly schematic fragmentary view of an in-line distillation system, which is constructed in accordance with the present invention;

FIG. 2 is a cross-sectional plan view of a trap for the system of FIG. 1 taken substantially along the line 2—2 thereof;

FIG. 3 is an enlarged, fragmentary, vertical cross-sectional rear elevational view of the trap of FIG. 1; and FIG. 4 is a cross-sectional elevational view of the distillation device for the system of FIG. 1 taken substantially along the line 4—4 thereof.

DETAILED DESCRIPTION

Referring now to the drawings, and more particularly to FIG. 1 thereof, there is shown an in-line distillation system 10, which is constructed in accordance with the present invention, and which facilitates the in-line continuous automatic testing of the concentration of volatile components entrained in a liquid. The system 10 generally comprises a distillation device generally indicated at 12 having an inlet 14 for receiving the liquid sample under pressure for flowing therethrough to an outlet 16, which is connected integrally in fluid communication with an inlet 17 of a T-distributor portion generally indicated at 18. For example, the liquid sample may be water having entrained hydrogen cyanide gas.

An upper conduit 20 is vertically disposed and is connected integrally in fluid communication with an upper port 21 of the distributor portion 18 to guide the separated volatile components flowing from the distillation device 12 through an upper reversely bent portion 23 of the conduit 20 to a horizontally extending mixing coil 22 having a second inlet 24 for introducing a suitable measured quantity of a liquid vehicle component, such as sodium hydroxide for mixing with the volatile component, such as hydrogen cyanide gas. An outlet 26 of the coil 22 guides the cyanide gas absorbed in the sodium hydroxide liquid to a suitable testing apparatus (not shown) for determining the concentration of the cyanides in the sodium hydroxide liquid vehicle. The vertical conduit 20 is sufficiently long to permit some cooling of the fluid flowing therethrough, but not sufficiently to cause the water vapor to condense and fall back downwardly because it is desired to have all of the water vapor condense in the mixing coil 22 so that substantially the same concentration of water condensation is contained in the samples to be tested. Thus, once the cooled water vapor and the volatile component flows through the bent portion 23 and flows downwardly into the coil 22, substantially the entire amount of water vapor and volatile component are retrieved for testing purposes.

A lower vertically extending conduit 28 connected in fluid communication with a lower outlet 29 of the distributor portion 18 forms a part of a trap generally indicated at 31 through which flows the wasted liquid from the distillation device 12. The trap 31 includes a tube or reservoir container 33 which receives the lower portion of the conduit 28, which extends through a neck 34 of the container 33. A stopper portion 35 is integrally formed concentrically about and axially aligned with the conduit 28 and is disposed sealingly and frictionally within the neck 34. As seen in FIG. 3 of the drawings, a tube 41 serves as an exit tube for the container 33 to permit the wasted liquid to flow therethrough. The tube 41 is reversely bent and is integrally connected at its inner end portion 43 (FIG. 3) to the upper end 35A of the stopper portion 35 in fluid communication therewith to guide the liquid flowing therethrough from a downwardly extending distal end portion 45, which is adapted to be connected in fluid communication with a drain line (not shown) or suitable storage container (not shown) for disposing of the wasted liquid. The tube 28 has a flared upper portion 28A to serve as a ball socket joint with the lower outlet 29 of the distributor portion 18 and extends downwardly and concentrically within the stopper portion 35 and the container 33 terminating at its exit end 28B spaced by a substantial distance above the bottom end wall 33A of the container 33 as shown in FIG. 2 of the drawing. With such a spacing, any sediment collecting within the container 33 does not clog the exit end 28B of the tube 28, since the trap 31 can be conveniently cleaned by removing the container from the stopper portion 35 and the tube 28 to permit the interior of the container 33 to be rinsed clean.

The stopper portion 35 is integrally connected at its closed upper end 35A to the tube 28 and is radially outwardly stepped and terminating in a downwardly depending, slightly tapered flange or skirt 35B which is adapted to engage sealingly and frictionally the inner surface of the neck portion 34. The axial length of the skirt 35B is substantially the same as the axial length of the neck portion 34. The entire trap 31 is preferably composed of suitable glass material since the liquids entering the trap are oftentime very hot in temperature and the glass material is capable of withstanding such temperatures after repeated use.

The system of the present invention is operated according to the segmented flow system, which is well known in the art and is mentioned in the above-mentioned publications, so that the various different samples are separated by trapped air or nitrogen gas to enable a series of samples to be tested in an in-line continuous manner by suitable conventional pumping equipment (not shown) to establish the segmented flow.

Considering now the distillation device 12 in greater detail, the device 12 is a thin-film distillation device and includes a glass tube 47 extending between the inlet 14 and the outlet 16. The inlet is gently upwardly turned and tapered to be connected in fluid communication with the segmented flow supply pump (not shown). The inlet is tapered because the tubing (not shown) to which it is connected is smaller in diameter than the diameter of the tube 47, and it is upturned so that the fluid flows downwardly into the tube 47. An aluminum bar 49 has a longitudinally extending groove 52 extending along the upper surface thereof for receiving the lower half portion of the glass tube 47. A hole 54 extends axially into the front end of the bar 49 for receiving an electric heating element 56 connected to a suitable source of electrical power by means of an electric cord 58 for heating the bar 49 to in turn heat uniformly the glass tube 47. In this manner, the heat is transferred uniformly from the heating element 56 to the glass tube 47 via the aluminum bar 49. Thus, by uniform heating of the glass tube 47, the thin-film distillation process is greatly facilitated. A similar hole 61 in the rear end of the bar 49 is adapted to receive a thermometer (not shown) to monitor the temperature of the bar.

The tube 47 is inclined slightly from its inlet 14 toward its outlet 16 by about five degrees.

The tubing for the system is composed of borosilicate glass tubing. The temperature is controlled by varying the current flow to the heating element, and can be monitored by continuously or periodically by a thermometer (not shown) mounted within the bar 49 to facilitate the fluid flow therethrough. The bar 49 and the remaining portion of the system 10 are supported by any suitable means (not shown).

Before commencing the operation of the system, the volume of the liquid flowing through the distillation device 12 can be measured by collecting the overflow from the tube 45 for a certain period of time (10 minutes). The heating is set and controlled by varying the current to the heating element 54. After equilibrium is reached, the wasted liquid flowing from the tube 45 is collected for an equal time period. The volume is measured after the liquid cools down to room temperature. Thus, the evaporated liquid volume is the difference between the total volume (on cold) and the wasted volume at the equilibrated set temperature, and $$\text{The Distillation Ratio} = \frac{\text{Evaporated Volume}}{\text{Total Volume}} \times 100$$

When the system is used for cyanide analysis in water and waste water, it is set into operation, and the temperature of the heating aluminum bar is adjusted to approximately 125° C., so that a distillation ratio of about 15–20% or as desired for a particular volatile component is maintained. The continuous flow contains a high ratio of air (or nitrogen) to liquid (6:1 as cold volumes)

as a result of the segmented flow to help the acidified sample to spread as a thin film into the heated glass tube. The volatile components, HCN and some water vapor, are stripped off and carried over to the absorption glass coil 22. An absorbing solution (NaOH) is continuously fed into the absorption coil at 24 to absorb, cool and condense the volatile components, which are then resampled to the rest of the automated system (not shown) for measurement. This is done colorimetrically, in the case of cyanides as well as phenols, or can be accomplished by other suitable conventional techniques according to the volatile component of interest.

Should a large concentration of the volatile component have sufficient pressure to force its way into the trap against the liquid contained therein, thereby spoiling the sample, the container 33 refills itself automatically by the liquid from the next sample flowing therein, and thus the system need not be shut down to refill the trap. Also, the container 33 can be easily cleaned.

While the present invention has been shown and described in connection with a particular embodiment thereof, it will be understood that many changes and modifications of this invention may be made by those skilled in the art without departing from the true spirit and scope thereof. Accordingly, the appended claims are intended to cover all such changes and modifications as fall within the true spirit and scope of the present invention.

What is claimed is:

1. In an in-line distillation system for separating volatile components entrained in a given quantity of a series of samples of liquid to be tested, distillation means having a thin film distillation tube, said tube having an inlet and an outlet for separating the volatile components from the liquid in each sample, said tube engaging and being heated by metal heating bar means, said inlet receiving said samples of liquid; distribution means connected in fluid communication with said outlet of said distillation means and having an upwardly extending first conduit and a downwardly extending second conduit for flowing the separated volatile components from said outlet of said distillation means through said first conduit and for flowing liquid from the outlet of said distillation means through said second conduit; and trap means for resisting the flow of the separated volatile components from entering said second conduit, said trap means including an inner downwardly depending conduit having at its upper end an inlet disposed below said outlet of said distillation means and connected in fluid communication with the lower end portion of said second conduit, said trap means including container means at least partially surrounding said inner conduit for receiving liquid from said second conduit via said inner conduit, said container means having a bottom wall and having means defining an outlet means open to the atmosphere at the upper portion thereof spaced by a substantial distance above the exit end of said inner conduit so that liquid from said distillation means fills said inner conduit and said container means to impede the flow of the separated volatile components into said second conduit and flows from the container outlet, said container means being substantially larger in cross section than the cross section of said inner conduit to permit liquid and any spurious volatile components flowing from said distillation means through said second conduit into said inner conduit to flow freely from the exit end of said inner conduit to the outlet of said container means, said trap means having a member for connecting said inner conduit sealingly and removably to said container means for facilitating disassembly of said trap means for cleaning purposes, said exit end of said inner conduit being unobstructed and spaced by a substantial distance above the bottom wall of said container means to provide a space therebetween to permit the collection of sediment material and thus to inhibit accumulations thereof from blocking the flow of liquid through said trap means, and condensing means for retrieving for testing purposes substantially the entire amount of said volatile component and liquid vapor received from said distillation means via said first conduit.

2. In an in-line distillation system according to claim 1, wherein said distillation conduit is inclined slightly from the horizontal toward said distribution means with its outlet end portion disposed lower than its inlet end portion.

3. In an in-line distillation system according to claim 1, wherein said container means contains an elongated tube having a closed end forming said bottom wall and having an open neck portion, said inner conduit having a stopper portion integrally connected thereto forming said member for engaging sealingly the inner surface of said neck portion, said outlet of said container means being a reversely bent tube integrally connected at one of its ends to said stopper portion in fluid communication therewith, said stopper portion having a downwardly depending skirt for engaging sealingly and frictionally the inner surface of said neck portion.

4. In an in-line distillation system according to claim 1, wherein said distribution means includes a T-connection portion.

5. In an in-line distillation system according to claim 1, wherein the liquid is water, the volatile component is hydrogen cyanide gas, and said liquid vehicle component is sodium hydroxide.

6. In an in-line distillation system according to claim 1, wherein said inner conduit is disposed in line with its inlet and with said second conduit to provide an uninterrupted, continuous, substantially linearly-configured passage for fluid flow through said inner conduit to its exit end.

7. In an in-line distillation system according to claim 1, further including a bent conduit portion interconnecting in fluid communication said condensing means and said first conduit.

8. In an in-line distillation system according to claim 1, wherein said distillation means further includes an electric heating element for heating the metal bar.

9. In an in-line distillation system according to claim 8, wherein said metal heating bar means includes a longitudinally extending open groove for receiving the bottom portion of said distillation tube for applying heat to it from said heating element.

* * * * *